(12) United States Patent
Weiser et al.

(10) Patent No.: US 6,986,784 B1
(45) Date of Patent: Jan. 17, 2006

(54) IMPLANT ANCHOR SYSTEMS

(75) Inventors: Michael F. Weiser, Groton, MA (US); Richard A. Gambale, Tyngsboro, MA (US); Stephen J. Forcucci, Medford, MA (US); Sean Forde, Watertown, MA (US); Kellywan Kan, Dracut, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/743,695

(22) PCT Filed: May 12, 2000

(86) PCT No.: PCT/US00/13118

§ 371 (c)(1),
(2), (4) Date: Apr. 12, 2001

(87) PCT Pub. No.: WO00/69345

PCT Pub. Date: Nov. 23, 2000

Related U.S. Application Data

(60) Provisional application No. 60/134,331, filed on May 14, 1999, provisional application No. 60/134,572, filed on May 17, 1999.

(51) Int. Cl.
*A61F 2/06* (2006.01)

(52) U.S. Cl. .............. 623/1.1; 623/1.14; 623/1.15; 623/1.23; 623/1.3; 606/108

(58) Field of Classification Search .......... 623/1.1, 623/1.11, 1.14, 1.15, 1.23, 1.33, 11–12, 900, 623/1.3, 1.31, 23.7, 23.66, 23.64; 606/108, 606/185, 195, 198, 208
See application file for complete search history.

(56) References Cited

U.S. PATENT DOCUMENTS

| | | | |
|---|---|---|---|
| 3,991,750 A | 11/1976 | Vickery | |
| 3,995,617 A | 12/1976 | Watkins et al. | |
| 4,130,904 A | * 12/1978 | Whalen | |
| 4,307,722 A | 12/1981 | Evans et al. | |
| 4,503,569 A | 3/1985 | Dotter | |
| 4,546,499 A | 10/1985 | Possis | |

(Continued)

FOREIGN PATENT DOCUMENTS

DE 19703482 1/1997

(Continued)

OTHER PUBLICATIONS

U.S. Appl. No. 09/073,118, filed May 5, 1998, Gambale.

(Continued)

*Primary Examiner*—Vincent Millin
*Assistant Examiner*—Lalita M. Hamilton
(74) *Attorney, Agent, or Firm*—Kirkpatrick & Lockhart Nicholson Graham LLP

(57) ABSTRACT

The present invention provides anchoring mechanisms for tissue implants. The anchors are integrated as part of the structure of the implant and serve to resist migration of the implant from highly dynamic muscle tissue such as the myocardium of the heart. In implant devices configured as a flexible coil, various attributes of the coil may be altered to increase the anchoring capability of the device. The flexibility of the device may be increased to resist migration by changing the coil filament thickness, pitch or filament material. Alternatively, the end coil may be altered to have a broader cross-sectional profile in engagement with the tissue or may include an anchoring barb. Additionally, methods of implanting a tissue implant device are provided.

47 Claims, 7 Drawing Sheets

U.S. PATENT DOCUMENTS

| | | | |
|---|---|---|---|
| 4,562,597 A | 1/1986 | Possis et al. | |
| 4,580,568 A | 4/1986 | Gianturco | |
| 4,582,181 A | 4/1986 | Samson | |
| 4,641,653 A | 2/1987 | Rockey | |
| 4,649,922 A | 3/1987 | Wiktor | |
| 4,655,771 A | 4/1987 | Wallsten | |
| 4,658,817 A | 4/1987 | Hardy et al. | |
| 4,665,918 A | 5/1987 | Garza et al. | |
| 4,681,110 A | 7/1987 | Wiktor | |
| 4,733,665 A | 3/1988 | Palmaz | |
| 4,768,507 A | 9/1988 | Fischell et al. | |
| 4,774,949 A | 10/1988 | Fogarty | |
| 4,813,925 A | 3/1989 | Anderson, Jr. et al. | |
| 4,861,330 A | 8/1989 | Voss | |
| 4,889,137 A | 12/1989 | Kolobow | |
| 4,904,264 A | 2/1990 | Scheunemann | |
| 4,917,666 A | 4/1990 | Solar et al. | |
| 4,920,980 A | 5/1990 | Jackowski | |
| 4,950,227 A | 8/1990 | Savin et al. | |
| 4,995,857 A | 2/1991 | Arnold | |
| 4,997,431 A | 3/1991 | Isner et al. | |
| 5,040,543 A | 8/1991 | Badera et al. | |
| 5,042,486 A | 8/1991 | Pfeiler et al. | |
| 5,047,028 A | 9/1991 | Qian | |
| 5,049,138 A | 9/1991 | Chevalier et al. | |
| 5,056,517 A | 10/1991 | Fenici | |
| 5,087,243 A | 2/1992 | Avitall | |
| 5,098,374 A | 3/1992 | Othel-Jacobsen et al. | |
| 5,114,414 A | 5/1992 | Buchbinder | |
| 5,158,548 A | 10/1992 | Lau et al. | |
| 5,167,614 A | 12/1992 | Tessmann et al. | |
| 5,176,626 A | 1/1993 | Soehendra | |
| 5,180,366 A | 1/1993 | Woods | |
| 5,190,058 A | 3/1993 | Jones et al. | |
| 5,256,146 A | 10/1993 | Ensminger et al. | |
| 5,266,073 A | 11/1993 | Wall | |
| 5,287,861 A | 2/1994 | Wilk | |
| 5,290,295 A | 3/1994 | Querals et al. | |
| 5,312,456 A | 5/1994 | Reed et al. | |
| 5,324,325 A | 6/1994 | Moaddeb | |
| 5,366,493 A | 11/1994 | Scheiner et al. | |
| 5,372,600 A | 12/1994 | Beyar et al. | |
| 5,380,316 A | 1/1995 | Aita et al. | |
| 5,389,096 A | 2/1995 | Aita et al. | |
| 5,391,199 A | 2/1995 | Ben-Haim | |
| 5,409,004 A | 4/1995 | Sloan | |
| 5,409,019 A | 4/1995 | Wilk | |
| 5,423,885 A | 6/1995 | Williams | |
| 5,425,757 A | 6/1995 | Tiefenbrun et al. | |
| 5,429,144 A | 7/1995 | Wilk | |
| 5,441,516 A | 8/1995 | Wang et al. | |
| 5,452,733 A | 9/1995 | Sterman | |
| 5,453,090 A | 9/1995 | Martinez et al. | |
| 5,458,615 A | 10/1995 | Klemm | |
| 5,464,404 A | 11/1995 | Abela et al. | |
| 5,464,650 A | 11/1995 | Berg et al. | |
| 5,466,242 A | 11/1995 | Mori | |
| 5,476,471 A * | 12/1995 | Shifrin et al. | 606/151 |
| 5,476,505 A | 12/1995 | Limon | |
| 5,480,422 A | 1/1996 | Ben-Haim | |
| 5,484,424 A * | 1/1996 | Cottenceau et al. | 604/525 |
| 5,487,739 A | 1/1996 | Aebischer et al. | |
| 5,514,176 A | 5/1996 | Bosley, Jr. et al. | |
| 5,536,274 A * | 7/1996 | Neuss | 623/1.22 |
| 5,551,427 A | 9/1996 | Altman | |
| 5,551,954 A | 9/1996 | Buscemi et al. | |
| 5,562,619 A | 10/1996 | Mirarchi et al. | |
| 5,562,622 A | 10/1996 | Tihon | |
| 5,562,922 A | 10/1996 | Lambert | |
| 5,569,272 A | 10/1996 | Reed et al. | |
| 5,571,168 A | 11/1996 | Toro | |
| 5,593,412 A | 1/1997 | Martinez et al. | |
| 5,593,434 A | 1/1997 | Williams | |
| 5,602,301 A | 2/1997 | Field | |
| 5,613,981 A * | 3/1997 | Boyle et al. | |
| 5,614,206 A | 3/1997 | Randolph et al. | |
| 5,643,308 A | 7/1997 | Markman | |
| 5,653,756 A | 8/1997 | Clarke et al. | |
| 5,653,759 A * | 8/1997 | Hogan et al. | |
| 5,655,548 A | 8/1997 | Nelson | |
| 5,662,124 A | 9/1997 | Wilk | |
| 5,676,850 A | 10/1997 | Reed et al. | |
| 5,690,643 A | 11/1997 | Wijay | |
| 5,735,897 A | 4/1998 | Buirge | |
| 5,738,654 A | 4/1998 | Tihon | |
| 5,741,330 A | 4/1998 | Brauker et al. | |
| 5,744,515 A | 4/1998 | Clapper | |
| 5,755,682 A | 5/1998 | Knudson et al. | |
| 5,756,127 A | 5/1998 | Grisoni et al. | |
| 5,762,600 A | 6/1998 | Bruchman et al. | |
| 5,769,843 A | 6/1998 | Abela et al. | |
| 5,782,823 A | 7/1998 | Mueller | |
| 5,785,702 A | 7/1998 | Murphy et al. | |
| 5,792,453 A | 8/1998 | Hammond et al. | |
| 5,797,870 A | 8/1998 | March et al. | |
| 5,807,384 A | 9/1998 | Mueller | |
| 5,810,836 A * | 9/1998 | Hussein et al. | |
| 5,824,049 A | 10/1998 | Ragheb et al. | |
| 5,824,059 A * | 10/1998 | Wijay | |
| 5,824,071 A | 10/1998 | Nelson et al. | |
| 5,830,502 A | 11/1998 | Dong et al. | |
| 5,840,059 A | 11/1998 | March et al. | |
| 5,861,032 A | 1/1999 | Subramaniam | |
| 5,879,383 A | 3/1999 | Bruchman et al. | |
| 5,891,133 A * | 4/1999 | Murphy-Chutorian | |
| 5,893,869 A * | 4/1999 | Barnhart et al. | 606/200 |
| 5,899,915 A | 5/1999 | Saadat | |
| 5,911,717 A * | 6/1999 | Jacobsen et al. | 606/1 |
| 5,971,993 A | 10/1999 | Hussein | |
| 5,980,514 A | 11/1999 | Kupiecki et al. | |
| 5,980,548 A | 11/1999 | Evans et al. | |
| 6,007,544 A * | 12/1999 | Kim | |
| 6,045,565 A | 4/2000 | Ellis et al. | |
| 6,053,924 A | 4/2000 | Hussein | |
| 6,059,825 A * | 5/2000 | Hobbs et al. | 623/1.18 |
| 6,197,324 B1 | 3/2001 | Crittenden | |
| 6,248,112 B1 | 6/2001 | Gambale et al. | |
| 6,251,418 B1 | 6/2001 | Ahern et al. | |
| 6,263,880 B1 | 7/2001 | Parker et al. | |
| 6,277,082 B1 | 8/2001 | Gambale | |
| 6,432,126 B1 | 8/2002 | Gambale et al. | |
| 6,447,522 B2 | 9/2002 | Gambale et al. | |
| 6,458,092 B1 | 10/2002 | Gambale et al. | |

FOREIGN PATENT DOCUMENTS

| | | |
|---|---|---|
| DE | 29619029 | 4/1997 |
| EP | 0 515 867 A2 | 12/1992 |
| EP | 0 490 459 A1 | 10/1994 |
| EP | 0 714 640 A1 | 6/1996 |
| EP | 0 717 969 A2 | 6/1996 |
| EP | 0 732 089 A2 | 9/1996 |
| EP | 0 812 574 A2 | 12/1997 |
| EP | 0 830 873 A2 | 3/1998 |
| EP | 0 853 921 A2 | 7/1998 |
| EP | 0 953 320 A2 | 11/1999 |
| EP | 1 062 920 A1 | 12/2000 |
| EP | 1062920 A1 | 12/2000 |
| EP | 1321111 A2 | 6/2003 |
| FR | 1514319 | 1/1967 |
| FR | 2725615 | 10/1994 |
| RU | 2026640 C1 | 1/1995 |
| RU | 2063179 C1 | 7/1996 |
| WO | WO 89/01798 | 3/1989 |

| | | |
|---|---|---|
| WO | WO 91/15254 | 10/1991 |
| WO | WO 94/05265 | 3/1994 |
| WO | WO 94/27612 | 12/1994 |
| WO | WO 96/20698 | 7/1996 |
| WO | WO 97/32551 | 9/1997 |
| WO | WO 97/38730 | 10/1997 |
| WO | WO 97/42910 | 11/1997 |
| WO | WO 97/44071 | 11/1997 |
| WO | WO 97/45105 | 12/1997 |
| WO | WO 97/47253 | 12/1997 |
| WO | WO 98/05307 | 2/1998 |
| WO | WO 98/08456 | 3/1998 |
| WO | WO 98/16644 | 4/1998 |
| WO | WO 98/23228 | 6/1998 |
| WO | WO 98/25533 | 6/1998 |
| WO | WO 98/29148 | 7/1998 |
| WO | WO 98/32859 | 7/1998 |
| WO | WO 98/46115 | 10/1998 |
| WO | WO 99/21510 | 5/1999 |
| WO | WO 99/38459 | 8/1999 |
| WO | WO 99/53863 | 10/1999 |

OTHER PUBLICATIONS

U.S. Appl. No. 09/159,834, filed Sep. 24, 1998, Cafferata.
U.S. Appl. No. 09/162,547, filed Sep. 29, 1998, Gambale.
U.S. Appl. No. 09/211,332, filed Dec. 15, 1998, Gambale et al.
U.S. Appl. No. 09/299,795, filed Apr. 26, 1999, Ahern.
U.S. Appl. No. 09/328,808, filed Jun. 9, 1999, Ahern.
U.S. Appl. No. 09/368,119, filed Aug. 4, 1999, Tedeschi et al.
U.S. Appl. No. 09/743,726, filed Apr. 12, 2001, Gambale et al.
U.S. Appl. No. 09/774,319, filed Jan. 31, 2001, Gambale et al.
U.S. Appl. No. 09/774,320, filed Jan. 31, 2001, Gambale et al.
U.S. Appl. No. 09/888,757, filed Jun. 25, 2001, Ahern et al.
U.S. Appl. No. 09/990,644, filed Nov. 21, 2001, Gambale et al.
U.S. Appl. No. 10/048,205, filed May 2, 2002, Gambale.
U.S. Appl. No. 10/048,694, filed Jun. 10, 2002, Gambale et al.
A. Hassan Khazei et al., "Myocardial Canalization, A new Method of Myocardial Revascularization", *The Annals of Thoracic Surgery*, vol. 6, No. 2, pp. 163-171, Aug. 1968.
Alfred Goldman et al., "Experimental Methods for Producing a Collateral Circulation to the Heart Directly from the Left Ventricle", *Journals of Thoracic Surgery*, vol. 31, No. 3, pp. 364-374, Mar. 1956.
A. Sachinopoulou et al., "Invited Review Transmyocardial Revascularization", *Lasers in Medical Science*, 1995, vol. 10, pp. 83-91, Sep. 1995.
B. Schumacher et al., Induction of Neoangiogenesis in Ischemic Myocardium by Human Growth Factors, First Clinical Results of a New Treatment of Coronary Heart Disease, Clinical Investigation and Reports, pp. 645-650, Dec. 1997.
Charles T. Dotter, Transluminally-placed Coilspring Endarterial Tube Grafts: Long-term Patency in Canine Popliteal Artery, Investigative Radiology, pp. 329-332, Sep.-Oct. 1969.
C. Massimo, et al., Myocardial Revascularization By a New Method of Carrying Blood Directly from the Left Ventricular Cavity into the Coronary Circulation, Journals of Thoracic Surgery, vol. 34, No. 2, pp. 257-264, Aug. 1957.

Garrett Lee et al., Feasibility of Intravascular Laser Irradiation for In vivo Visualization and therapy of Cardiocirculatory Diseases, American Heart Journal., vol. 103 No. 6, pp. 1076-1077.
Garrett Lee et al., Laser-Dissolution of Coronary Atherosclerotic Obstruction, American Heart Journal, vol. 102, No. 6, part 1, pp. 1074-1075, Dec. 1981.
George S. Abela et al., Use of Laser Radiation to Recanalize Totally Obstructed Coronary Arteries (Abstract), Journal American College Cardiology 1983: 1(2):691.
George S. Abela et al., Laser Revascularization: What Are Its Prospects?, Journal of Cardiovascular Medicine, pp. 977-984, Sep. 1983.
Isam N. Anabtawi et al., Experimental Evaluation of Myocardial Tunnelization as a Method of Myocardial Revascularization, Journal of Thoracic and Cardiovascular Surgery, vol. 58, No. 5, pp. 638-646, Nov. 1969.
John E. Hershey et al., Transmyocardial Puncture Revascularization, Geriatrics, pp. 101-108, Mar. 1969.
Ladislav Kuzela et al. Experimental Evaluation of Direct Transventricular Revascularization, Journal of Thoracic Cardivascular Surgery, vol. 57, No. 6, pp. 770-773, Jun. 1969.
Mahmood Mirhoseini et al., Myocardial Revascularization by Laser: A Clinical Report; Lasers in Surgery and Medicine 3:241-245 (1983).
Mahmood Mirhoseini et al. Revascularization of the Heart by Laser; Journal of Microsurgery, pp. 253-260, Jun. 1981.
Mahmood Mirhoseini et al., Transventricular Revascularization by Laser, Lasers in Surgery and Medicine, vol., 2, pp. 1987-1998, 1982.
Mahmood Mirhoseini et al., Clinical Report: Laser Myocardial Revascularization, Lasers in Surgery and Medicne, vol., 6, pp. 459-461, 1986.
Mahmood Mirhoseini et al., New Concepts in Revascularziation of the Myocardium, The Annals of Thoracic Surgery, vol. 45, No. 4, pp. 415-420, Apr. 1988.
P. Walter et al., Treatment of Acute Myocardial Infarction by Transmural Blood Supply from the Ventricular Cavity, Department of Surgery and Department of Radiology of the Hanover Medical School, Hanover, pp. 130-138, (1971).
Peter Whittaker, et al., Transmural Channels Can Protect Ischemic Tissue, Assessment of Long-term Myocardial Response to Laser and Needle-Made Channels, Circulation, vol. 93, No. 1, pp. 143-152, Jan. 1996.
P.K. Sen. et al., Further Studies in Multiple Transmyocardial Acupuncture as a Method of Myocardial Revascularization, Surgery, vol., 64, No. 5, pp. 861-870, No. 1968.
P.K. Sen, et al, Transmyocardial Acupuncture, A New Approach to Myocardial Revascularization; Journal of Thoracic and Cardiovascular Surgery, vol. 50, No. 2, pp. 181-189, Aug. 1965.
R.I. Hardy et al., Regional Myocardial Blood Flow and Cardiac Mechanics in Dog Hearts with $CO_2$ Laser-Induced Intramyocardial Revascularization, Basic Research Cardiology, 85:179-197 (1990).
Roque Pifarre et al., Myocardial Revascularization by Transmyocardial Acupuncture: A Physiologic Impossibility; Journal of Thoracic and Cardiovascular Surgery; vol. 58, No. 3, pp. 424-429, Sep. 1969.
Valluvan Jevanandam et al., Myocardial Revascularization by Laser-Induced Channels, Surgical Forum vol. VL, American College of Surgeons 76th Clinical Congress, vol. 4, pp. 225-227, Oct. 1990.

Neil B. Ingels, et al., Measurement of Midwall Myocardial Dynamics in Intact Man by Radiography of Surgically Implanted Markers, Circulation, vol. 52, pp. 859-867 (Nov. 1975).

* cited by examiner

IMPLANT ANCHOR SYSTEMS

RELATED APPLICATION

This application is a §371 national stage application of PCT/US00/13118, which claims priority to U.S. provisional application Ser. Nos. 60/134,331 filed May 14, 1999 and 60/134,572 filed May 17, 1999.

FIELD OF THE INVENTION

This invention relates to tissue implant devices and methods of their use. In particular, the devices and methods concern systems for anchoring the implants in tissue so that they do not migrate after implantation.

BACKGROUND OF THE INVENTION

There are a variety of applications for tissue implant devices in the human body. Such applications include electrical pacing leads or other tissue monitoring devices or tissue support structures such as endoluminal stents. A device implanted in tissue may experience migratory forces applied by movement of the surrounding tissue into which the device has been implanted. Migration is especially a problem in muscle tissue that regularly contracts and relaxes around the device. Because the device is static and is relatively inflexible, rather than absorbing the forces applied by the tissue, those forces act on the device to move it in the tissue. Migration of the device ultimately may lead to ejection of the device from the tissue. An ejected device could prove harmful to a patient if it enters the blood stream and blocks blood flow to a critical organ such as the brain.

Perhaps the most regular aggressive migratory forces created by muscle tissue may be experienced by implant devices which are placed in heart tissue. Because the heart muscle regularly contracts and relaxes in an exaggerated fashion to pump blood through the ventricle, implant devices located within that tissue have significant forces applied upon them. For example, the myocardial tissue comprising the exterior wall of the heart at the left ventricle may increase in thickness by forty to sixty percent with each contraction. Conventional methods of anchoring a device to tissue such as by stapling or suturing prove difficult in applications where there is exaggerated and constant movement of the subject tissue because it is difficult to accurately apply a suture or staple to the intended location.

Implant devices for the heart have been disclosed in U.S. Pat. No. 5,429,144 (Wilk) and in U.S. Pat. No. 5,810,836 (Hussein et al.) for the purpose of restoring blood flow to the tissue of the heart. Conventional treatments of restoring blood flow to heart tissue such as coronary artery bypass grafting have been supplanted in recent years by various methods of transmyocardial revascularization (TMR). TMR methods include creating channels into tissue of the heart either by needle acupuncture or coring with a hypodermic tube or by laser or mechanical ablative methods. Hussein and Wilk attempt to maintain the patency of such channels by a placement of a mechanical implant device to the heart tissue to support an open pathway through which blood may flow. The Hussein patent discloses several stent embodiments that are delivered through the epicardium of the heart into the myocardium and positioned to be open to the left ventricle.

Due to the exaggerated migration forces experienced by an implant device in heart tissue as described above, it would be desirable to provide devices and methods for securely anchoring an implant in an associated dynamic region of tissue. It is a general object of the present invention to provide such an anchoring system for tissue implants, especially those intended for placement in the heart that may be useful for revascularization of the heart tissue by various mechanisms.

SUMMARY OF THE INVENTION

The present invention provides implant devices configured to become anchored within tissue so that they do not migrate despite experiencing aggressive migration forces applied by the highly dynamic movement of muscle tissue that surrounds them. Additionally, methods for placing the devices so that they remain securely anchored within the tissue are provided. The devices are comprised of a flexible body, preferably formed from a helical wound spring.

The devices of the present invention not only exhibit improved anchoring effectiveness, but also are configured to provide better durability and resistance to possible fracture in a highly dynamic tissue environment. The system for anchoring also controls injury to the tissue in which the device is implanted. Although tissue injury and its associated injury response may be a mechanism of initiating beneficial angiogenesis in tissue, it is preferable to have control over the amount of injury created by implanting a device. The present anchoring systems provide the ability to reduce the trauma, tearing and injury to tissue that can be caused by anchoring a device to the tissue.

The devices of the present invention may be delivered to the intended tissue location percutaneously, through a catheter based system, transthoracically or surgically. Although the inventive devices and methods can be applied to implants intended for use in any region of the body, it is believed that the anchor systems are especially useful as applied to implant devices for the heart configured to treat ischemia. Flexible implant devices may be configured to promote angiogenesis through a variety of mechanisms examples of which are described in detail in pending U.S. patent application Ser. Nos. 09/164,173, 09/211,332 and 09/299,795.

Several embodiments of anchoring systems for flexible coil spring body implant devices formed from a filament are disclosed. Generally, the spring implant devices may be considered to have a body having proximal and distal portions. In the present application, proximal is understood to mean the direction leading external to the patient and distal is understood to mean any direction leading internally to the patient. The implant devices discussed herein are delivered into the tissue in a distal direction so that the body is implanted within the tissue and the proximal end of the device is approximately flush with the tissue surface or slightly submerged under the surface. In some embodiments the anchoring mechanism comprises an area of the device at its proximal portion or end having a profile that is larger than the profile of the distal portion of the device.

In a preferred embodiment, the anchoring tail at the distal portion of the device is configured to reside beneath the tissue surface after the device is implanted. The tail may comprise the proximal most coil of the device being flared outward to define an arm, perhaps curved, extending tangentially or spirally from the cylindrical profile of the implant device defined by the more distal coils of the device. The arm may be bent distally to provide a projecting edge for engaging tissue. The device can be implanted in tissue over an appropriate delivery device discussed in detail below by applying an insertion force while rotating the device so that it "screws" into the tissue. The device is advanced until the most proximal coil becomes submerged slightly under the tissue. The configuration of the arm appears to resist migration of the device either distally through the tissue or proximally back out of the tissue. Additionally, the arm appears to resist rotational movement of the device so that it does not "unscrew" out of the tissue. A bulbous tip at the proximal end of the device aids in resisting rotational movement of the device.

In another preferred embodiment, the anchor system comprises an increasing taper of the overall diameter of the device in the proximal direction. Particularly, the most proximal coils of the device increase in diameter size in the proximal direction to form a somewhat conical shape. The increasing taper may be present along the full length of the device or the most distal coils may be a constant diameter with the increasing taper in the proximal direction beginning at some point along the length of the device. As with the previous embodiment, the proximal portion of the device thus defines a profile that is greater than the profile of the distal portion of the device. As with the previous embodiment, the most proximal coil of the tapered device is submerged below the surface of the tissue when the device is implanted.

The configuration of the above-described embodiments offer distinct advantages over other anchoring mechanisms. Both the arm and the tapered embodiments do not require an abrupt transition in the filament shape to define a tail. An abrupt transition or bend in the filament may weaken the filament material causing it to break prematurely under the stresses created by dynamic loading of the surrounding tissue. Therefore, the absence of such a transition may be a distinct advantage and durability of the device. Additionally, because no more portion of the device extends above to the surface of the tissue, no segment of the device will lie across a transition region which may develop between the highly dynamic muscle tissue into which the device is implanted and a more static tissue surface which may be created if fibrous tissue develops at the surface of the tissue where the device is implanted. Additionally, the submerged proximal portion of the device serves to resist rotational movement of the device in the proximal direction.

In an alternate embodiment of the tissue implant device, a flexible coil spring body is configured to have a broadly wound proximal coil to serve as an anchoring tail. The broadly wound coil defines a larger profile than the more distal coils of the implant device. The broadly wound coil does not become submerged below the tissue surface when the device is implanted, but rather, remains flush with the surface to resist migration of the device in the distal direction. The broadly wound coil may be a continuation of the helical coil winding that forms the body of the device or it may be extended proximally from the body of the coil by a neck region. Because the broad wound coil has a profile that is larger than the body of the implant device, it tends to distribute migratory forces acting in the distal direction over a broader surface area of the tissue, preventing the tail from penetrating the tissue and allowing migration. The broad wound coil that serves as a tail may be circular or a variety of non-circular shapes. It may be provided with or without barbs to lock into the tissue. The tail may be concentric with or off center from the longitudinal axis defined by the coils that make up the body of the implant device. Additionally, the proximal end of the coil may be secured to the broad loop by wrapping welding or by crimping a malleable sleeve so that a closed loop configuration is maintained. The integrity of the proximal portion of the device that defines the tail may be enhanced by increasing the flexibility of the neck which joins the tail to the body with a coiled loop formed in the filament. Alternatively, the tail may be fortified by utilizing several coils abutting each other to form the broad loop.

In an alternative embodiment of the invention, a flexible implant device formed from a helical spring body may be formed from a filament having a non-circular cross-section. For example, a filament having a rectangular cross-section may serve to prevent migration through the tissue in the axle direction by several mechanisms. When the helical coil is wound such that the major axis of the rectangular cross-section is substantially perpendicular to the longitudinal axis of the body of the device greater axial flexibility is imparted to the spring, while maintaining sufficient radial stiffness to resist crushing by the tissue, then would be possible with a round cross-sectional filament material. Increased axial flexibility of the device permits it to move with surrounding tissue, absorbing forces that would otherwise tend to push the device out of position in the tissue. Additionally, as surrounding tissue herniates through the individual coils of the device, the orientation of the major axis of the rectangular cross-section of the filament to be perpendicular to the longitudinal axis of the device presents a larger surface area engaging the tissue to resist axial migration. Alternatively, the major axis of the rectangular cross-section filament may be oriented at an angle that is acute to the longitudinal axis of the device, so that the filament is canted in the proximal direction, to facilitate insertion of the device in the distal direction during implantation into the tissue. The canted orientation of the rectangular cross-sectional filament still provides the flexibility benefits of the perpendicular orientation discussed above and may enhance anchoring capability by presenting a leading proximal facing edge that serves to grip into tissue.

In another aspect of the present invention, tissue implant devices are anchored to the tissue with surgical adhesive. The surgical adhesive may be applied to the exterior device, similar to a coating prior to delivery, or may be applied to the device in tissue location after delivery. In the case of delivering adhesive after implantation, the delivery device may be configured to have a bore configured to deliver surgical adhesive to the interior device of the device after it has been implanted into tissue. Alternatively, the surgical adhesive may be applied directly to the proximal end of the device at the tissue surface interface manually, after delivery of the device. Tissue implant devices having a wide variety of configurations may be anchored using a surgical adhesive such as that disclosed in U.S. Pat. No. 4,057,535. Such an adhesive is biocompatible and absorbable. Ultraviolet curing adhesives may also be used, which form a structure after curing that is flexible and ultimately, absorbable.

In another aspect of the invention, the device is configured to resist migration in the tissue by exhibiting adequate flexibility in the axial direction to absorb migrational forces applied by surrounding tissue so that the device does not become displaced. As mentioned above in connection with the non-circular cross-sectional filament embodiment, the device can be configured to be adequately flexible in the axial direction while still providing sufficient radial stiffness to resist collapse of the device under force of the surrounding tissue. In the case of an implant device comprising a flexible helical spring body, variables such as filament diameter, spacing between individual coils and filament material may be altered to provide adequate axial flexibility in a device to reduce migration. For example, a variety of filament materials may be used such as surgical grade stainless steels. Other materials may be used to vary the modulus of elasticity of the filament. Additionally, flexibility of the coil implant may be varied along the length of the coil, not only by varying spacing between coils and diameter of the filament along its length, but also by using two or more different filament materials along the length of the filament that have different modulii of elasticity.

It is an object of the present invention to provide a tissue implant device that resists migration from the tissue into which it is implanted by offering improved anchoring capability.

It is another object of the present invention to provide a tissue implant device having an anchor mechanism that controls the amount of injury inflicted upon tissue at the implant site.

It is yet another object of the present invention to provide an implant device that resists migration by its inherent flexibility and ability to absorb migratory forces exerted by surrounding tissue.

It is another object of the invention to provide an implant device that utilizes an anchoring mechanism that is submerged beneath the surface of the tissue into which the device is implanted.

It is another object of the present invention to provide a tissue implant device that utilizes an anchor mechanism that resides flush with the tissue surface when the device is implanted.

It is yet another object of the invention to provide a method of implanting a tissue implant device so that it remains anchored in the tissue.

BRIEF DESCRIPTION OF THE DRAWINGS

The foregoing and other objects and advantages of the invention will be appreciated more fully from the following further description thereof, with reference to the accompanying diagramatic drawings wherein.

DESCRIPTION OF THE ILLUSTRATIVE EMBODIMENTS

Figure 1:
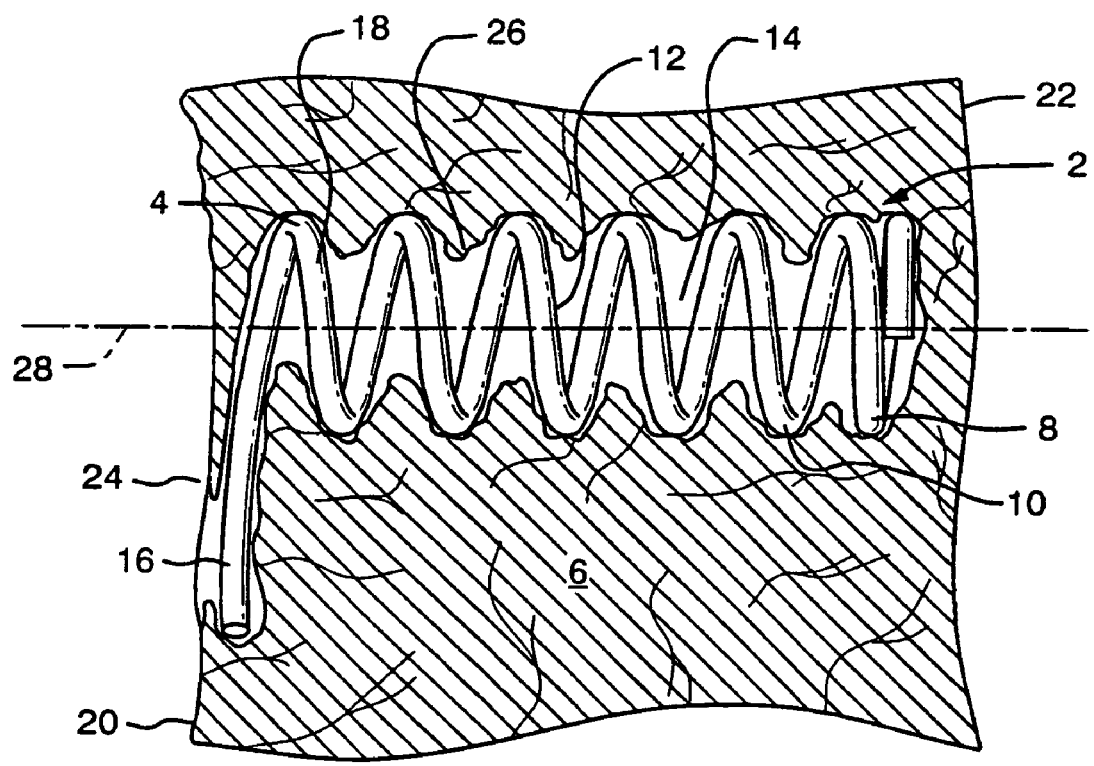
FIG. 1 is a highly diagrammatic illustration of a tissue implant device of the present invention implanted in tissue.

FIG. 1 shows a partial sectional side view of a preferred embodiment of an implant device configured for improved anchoring. The implant device 4 comprises a helical spring body 8 formed of a plurality of individual coils 10. The helical spring body 8 defines an interior 12 which maintains an open cavity 14 within the tissue 6 when the device is implanted. The anchor mechanism comprises a laterally extending arm, which extends from the most proximal coil 18 of the spring body 8 to define a lateral extent away from the longitudinal axis 28 of the device that is greater than the overall diameter of the coil body 8.

The implant device is particularly useful in treating ischemic tissue such as that often occurs in a myocardium of the heart. As shown in FIG. 1 the implant device may be inserted into the tissue 6, such as that of the myocardium, through the epicardial surface 20 at entry site 24 such that the device extends the majority of the thickness of the myocardium towards endocardial surface 22. Also, the device is fully implanted within the tissue such that the proximal laterally extending arm 16 is submerged within the tissue.

Figure 2:
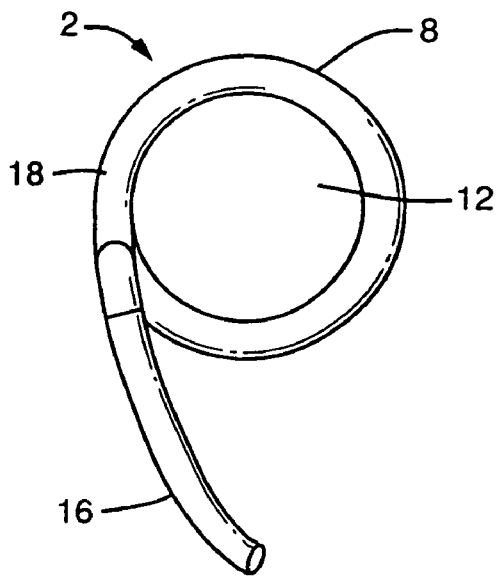
FIG. 2 is an end view of the tissue implant device shown in FIG. 1.

FIG. 2 shows an end view of the device 2 and in particular the laterally extending arm 16, which is configured to prevent migration of the device. As is seen in FIG. 2 the arm extends from the most proximal coil 18 in a tangential direction from the round coil. The arm 16 then curves slightly in the direction of the curvature of the coil. Preferably the lateral extent of the arm beyond the outside diameter of the device is approximately 1–3 mm. Generally the diameter of the body 8 of the coil is preferably on the order of 2–3 mm. The arm serves to provide increased surface area engaged with the tissue to prevent migration in an axial direction through the tissue. Furthermore, the implantation of the arm into the tissue causes it to prevent rotation of the device so that the device cannot back out of its tissue implant site.

Figure 3:
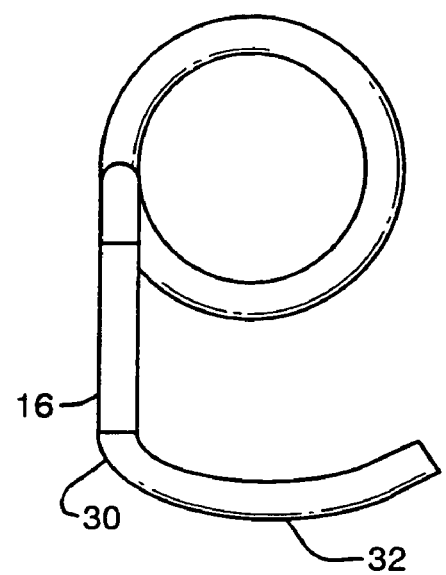
FIG. 3 is an end view of a modified version of the tissue implant device shown in FIG. 1.

FIG. 3 shows a variation of the laterally extending arm 16 having a bend 30 and second lateral extent 32. The alternate embodiment of the laterally extending arm 16 shown in FIG. 3 provides additional surface area and may serve additionally help to prevent rotation of the device. Variations of the shape of the laterally extending arm are possible and are considered within the scope of the invention.

Figure 4:
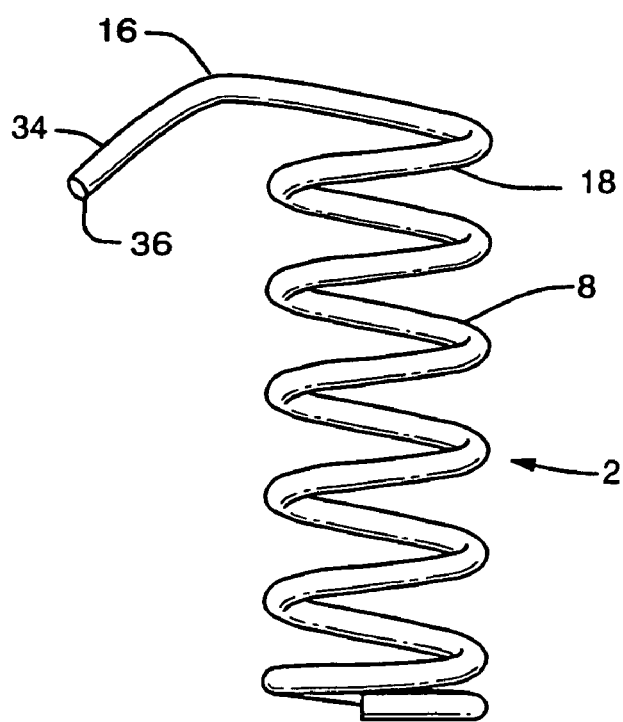
FIG. 4 is a side view of a modified version of the tissue implant device as shown in FIG. 1.

Another alternative design of the lateral extending arm is shown in FIG. 4. The lateral extending arm 16 is shown to have a distally projecting bend 34 at the proximal end 36 of the arm. The distally projecting bend 34 may serve to further resist axial movement in the distal direction when the device is implanted in tissue because it serves more as a barb to claw into the tissue to resist movement. The penetration of the bend also serves to resist rotation of the device. Alternatively, the bend 34 need not be as extreme as shown in FIG. 4, but rather the bend may be subtle, only to the extend that the arm 16 extends horizontally rather than following the acute angle of the helical pattern of the most distal coil 18.

Figure 5:
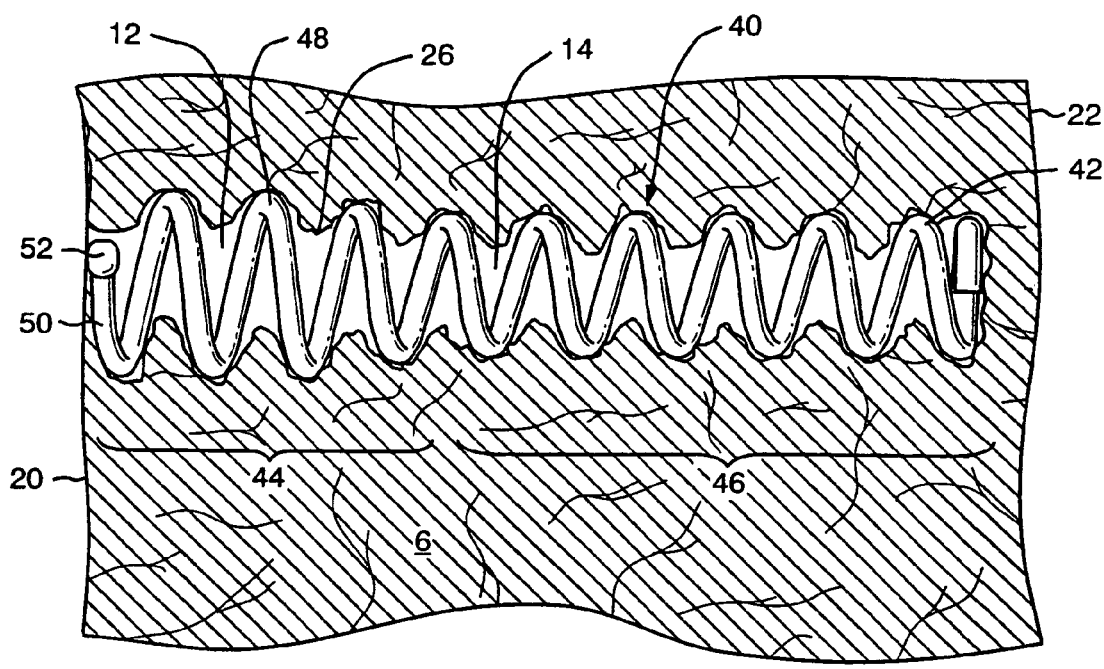
FIG. 5 is a highly diagrammatic illustration of a preferred embodiment of the tissue implant device of the present invention implanted in tissue.

FIG. 5 shows another preferred embodiment of the implant device. A semi-tapered coil spring implant device 40 may also provide adequate anchoring in dynamic tissue such as the tissue of the myocardium while meeting the objectives of the invention. The implant device 40 comprises a helical coil spring 42 having a proximal portion 44 and a distal portion 46. The individual coils 48 of the spring 42 increase in diameter through the proximal portion 44. Each coil increases in size in the proximal direction. However, the coils of the distal portion 46 are a constant diameter that is somewhat smaller than the diameter of the coils of the proximal portion. The most proximal coil 50 does not extend laterally outward as with the previous embodiment, rather it terminates in its position as part of the helical coil arrangement. The proximal end of the coil may be formed to have a bulbous shape 52 to further resist penetration of the tissue after the device has been implanted. As with the previous embodiment, the tissue tends to herniate at points 26 along the length of the implant. In experiments, the implant device 40 has shown to resist migration and rotation by virtue of the partial increase in taper at the proximal portion 44 of the device. This configuration may also serve to resist migration due to the enhanced flexibility of the proximal coils by virtue of their increased diameter. Increasing the overall diameter of the proximal coils (while maintaining the same filament thickness) serves to increase the flexibility of those coils.

Figure 6:
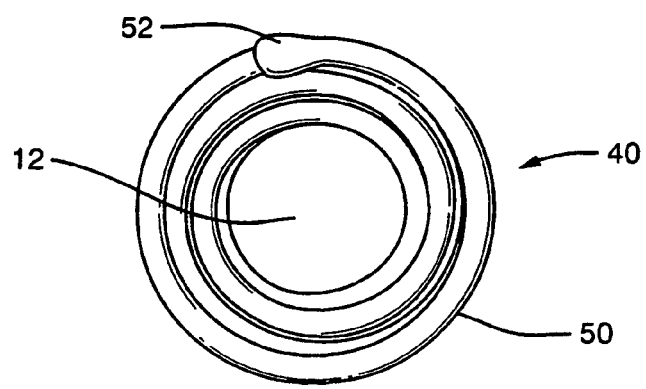
FIG. 6 is an end view of a preferred embodiment of the tissue implant device shown in FIG. 5.
Figure 7:
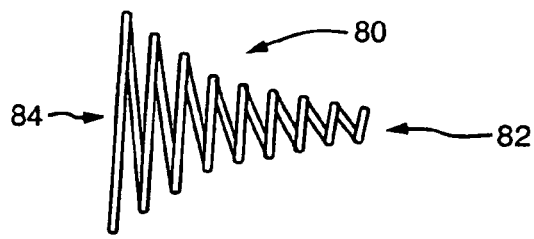
FIG. 7 is a side view of another preferred embodiment of the tissue implant device.

FIG. 6 shows an end view of the implant device 40 having a partial taper at the proximal portion 44. As with the first embodiment, the most proximal coil 50 is submerged within the tissue 6 when the device is implanted. The submersion of the most proximal coil provides the advantages detailed above and additionally avoids placing a section of the coil across the transition between the tissue and tissue surface, which may tend to move differently placing an increased stress on the device and possibly leading to premature failure. FIG. 7 shows a variation of the preferred embodiments discussed above wherein the increasing taper is present throughout the length of the device 80 such that each coil increases in diameter in a direction from the distal end 82 to the proximal end 84. The full taper embodiment 80 is believed to offer the same benefits as described in connection with the device shown in FIG. 5. In the above described tapered embodiments the smaller distal coils 46 may define a diameter on the order of approximately 2.2 millimeters measured to the outside diameter of the coils and the larger diameter, maximum extent of the taper may be on the order of 4,5 to 5 millimeters. The devices are preferably on the order of 7–8 mm in length.

Figure 8:
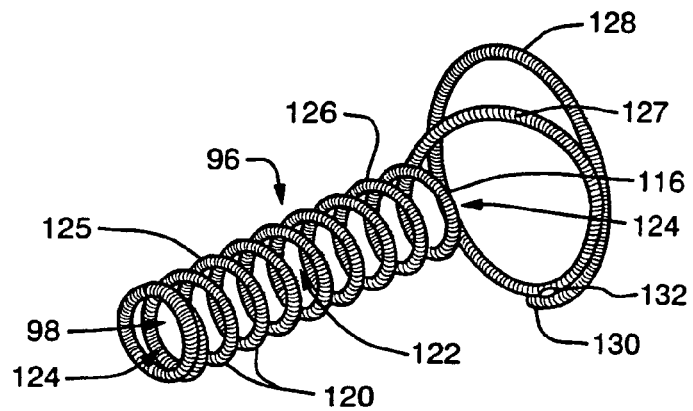
FIG. 8 is an isometric view of an alternate embodiment of the tissue implant device.

FIG. 8 shows an alternate embodiment of an implant device having an anchoring mechanism. The coil device has an interior 98, which is defined by the individual turns 120 of the coil. The helical coil 96 defines a frame, which holds back surrounding tissue so that blood may pool in the interior chamber, coagulate and become fibrin. Spaces 122 between individual turns of the coil permit communication between the interior chamber 98, where fibrin will grow and the blood and tissue that surround the device. Open ends 124 also permit communication between the interior chamber 98 and surrounding tissue. The coil 96 has a tail 128 configured to resist excessive penetration of the device into the subject tissue so that the overall depth that the device is implanted in the tissue is controlled. The tail 128 may be configured in a variety of forms. The example of a tail shown in FIG. 8 comprises a single broad coil joined to the main body 125 of the device by an extension neck 127, which may be a continuation of the most proximal coil 116. When the device is implanted in tissue, the broad coil of the tail is positioned to be flush with the surface of the tissue. The broad coil tail distributes the migratory forces experienced by the device over a broad area of tissue surface. The tail resists penetration of tissue surface thereby preventing migration of the device further into the tissue. Additionally, filament 126 from which the coil is formed may be a solid material or may, itself, be a coil spring structure having a plurality of openings between turns of the coil, which serve to permit herniation of surrounding tissue into the coil for anchoring capability. The broad coil tail 128 has a proximal end 130 which is preferably joined to the broad coil to maintain the coil circular shape. The proximal end 130 can be joined to the broad coil 128 by a variety of means such as welding as is shown by weld 132.

Figure 9:
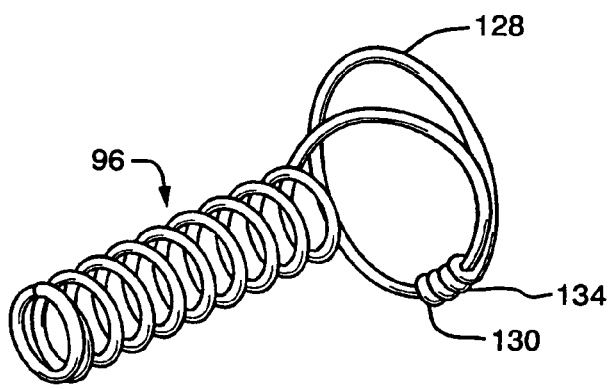
FIG. 9 is a isometric view of a variation of the alternate embodiment of the tissue implant device.
Figure 10:
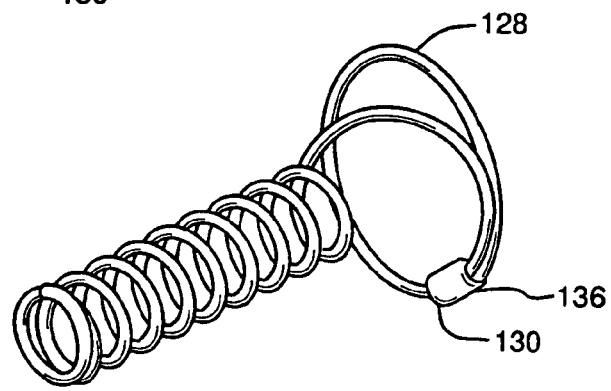
FIG. 10 is a isometric view of a variation of the alternate embodiment of the tissue implant device.

FIG. 9 shows an alternative embodiment of joining the proximal end 130 to the broad coil tail 128. The alternative embodiment comprises wrapping the portion of the filament adjacent the proximal end 130 around the broad coil tail 128 in several turns FIG. 10 shows another alternative embodiment useful for joining the proximal end 130 of the coil 96 to the broad coil tail 128. The alternative embodiment utilizes a malleable sleeve 136 to encompass both a portion of the broad coil tail 128 and the distal end of the coil 130. The malleable sleeve is then crimped to mechanically grasp the distal end 130 and broad coil and join them so that the circular shape of the broad coil tail 128 is maintained.

Figure 11:
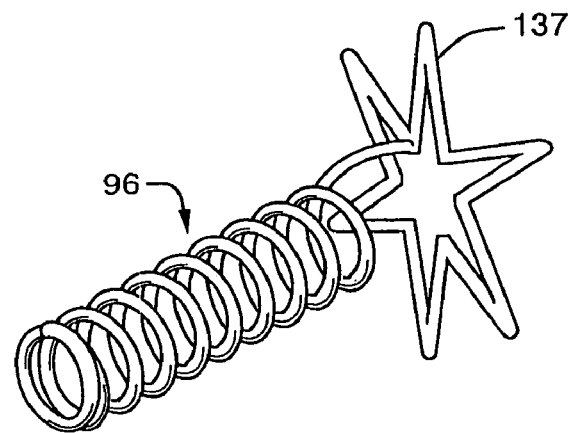
FIG. 11 is a isometric view of a variation of the alternate embodiment of the tissue implant device.
Figure 12:
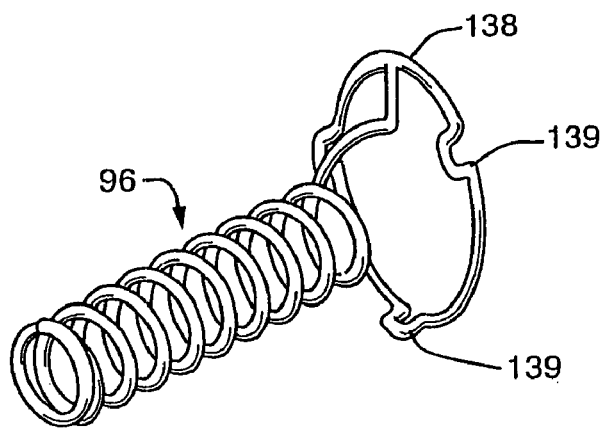
FIG. 12 is a isometric view of a variation of the alternate embodiment of the tissue implant device.

The broad coil tail 128 need not be a circular shape but may have a variety of broad shapes capable of serving to disperse migratory forces over a broad surface area of tissue when the device is implanted. FIG. 11 shows a possible non-circular shape for the broad coil comprising a star shaped 137. FIG. 12 shows yet another alternative embodiment for the shape of the broad coil tail 128. In FIG. 12 a somewhat oval broad coil 138 is shown. Additionally, the broad coil 138 has plurality of distally projecting protrusions 139, which may increase the grasp of the coil into the tissue to prevent migration.

Figure 13:
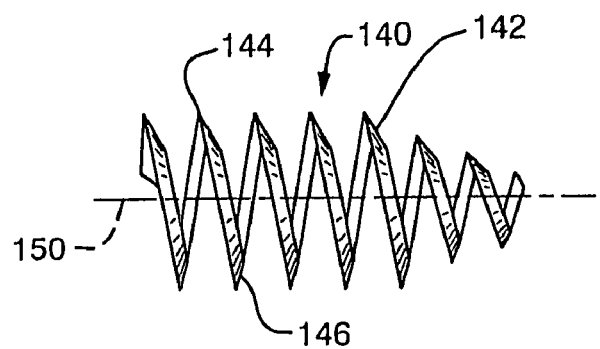
FIG. 13 is a side view of an alternate embodiment of the tissue implant device.
Figure 14:
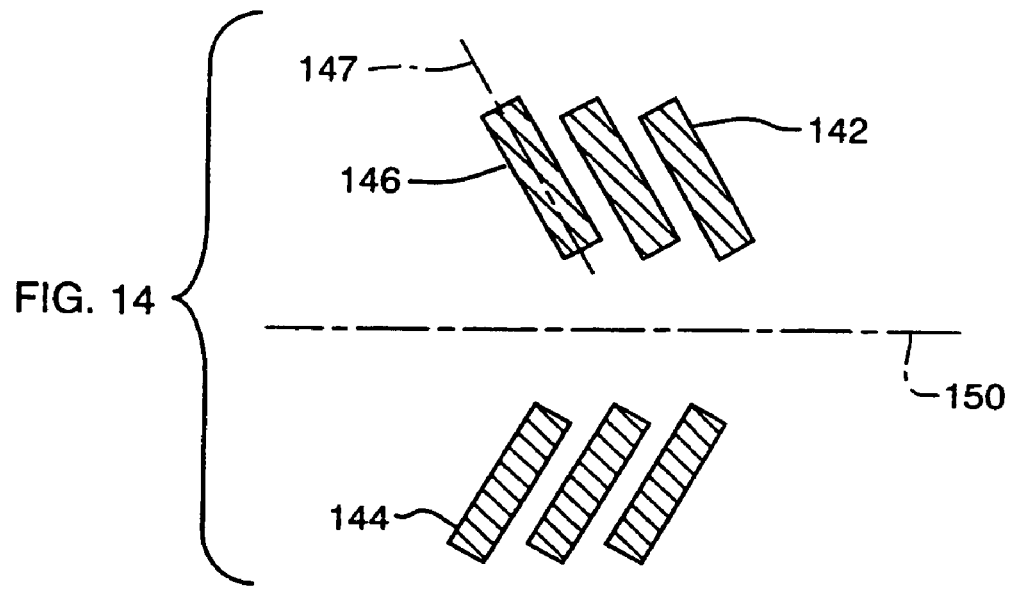
FIG. 14 is a partial sectional view of the tissue implant device shown in FIG. 13.

FIG. 13 shows yet another alternate embodiment of a tubular frame device. The canted coil device 140 is formed from a filament 142 of rectangular cross-section such as a strand of flat wire. As shown in FIG. 14, the coil is formed so that the major cross-sectional axis 147 of the rectangular wire is oriented at an acute angle to the longitudinal axis 150 of the coil 140. The orientation gives each turn 146 of the coil a projecting edge 144, which tends to claw into tissue to serve as an anchoring mechanism for the device.

Figure 15:
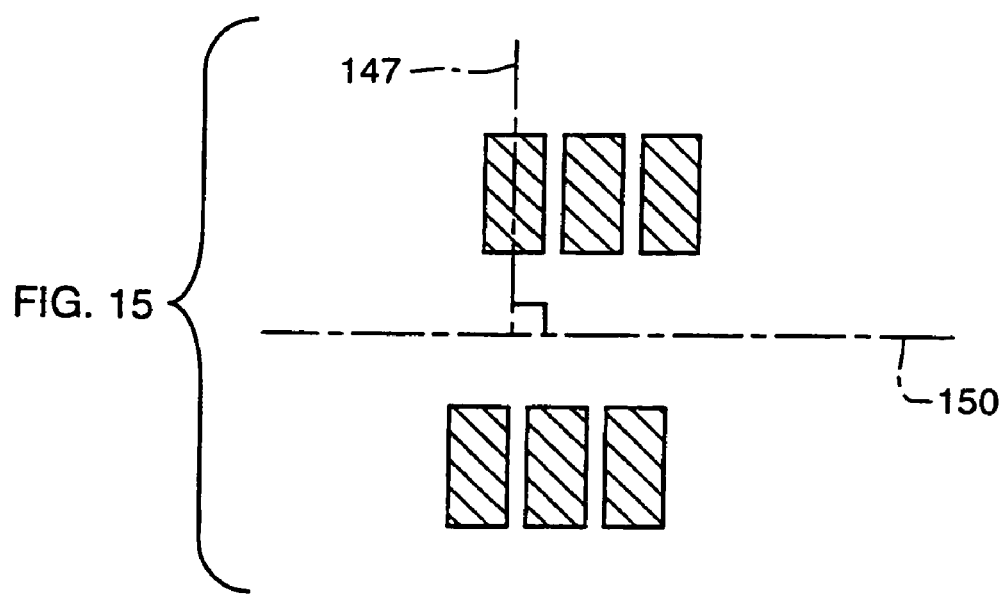
FIG. 15 is a partial sectional view of a variation of the tissue implant device shown in FIG. 13.

FIG. 15 shows a wrapped ribbon implant embodiment. The implant 90 is formed by a filament of a rectangular cross-sectional filament around a ribbed mandrel. In the present embodiment, the major axis 147 of the rectangular cross-section ribbon is oriented substantially perpendicular to the longitudinal axis 150 of the implant, as is shown in FIG. 15. In this configuration, the major axis 147 of the coils 142 of the rectangular ribbon do not extend radically from the longitudinal axis 150 of the implant 140 at an acute angle. With greater coil surface area extending away from the longitudinal axis of the implant, the implant is believed to be more stable and less likely to migrate once implanted within the myocardium. The implant is preferably formed from 316 stainless steel rectangular cross-section forming wire. Preferred dimensions for the rectangular cross-section filament are on the order of 0.003 inches to 0.005 inches for the minor axis width and 0.015 to 0.018 inches for the major axis.

Figure 16A:
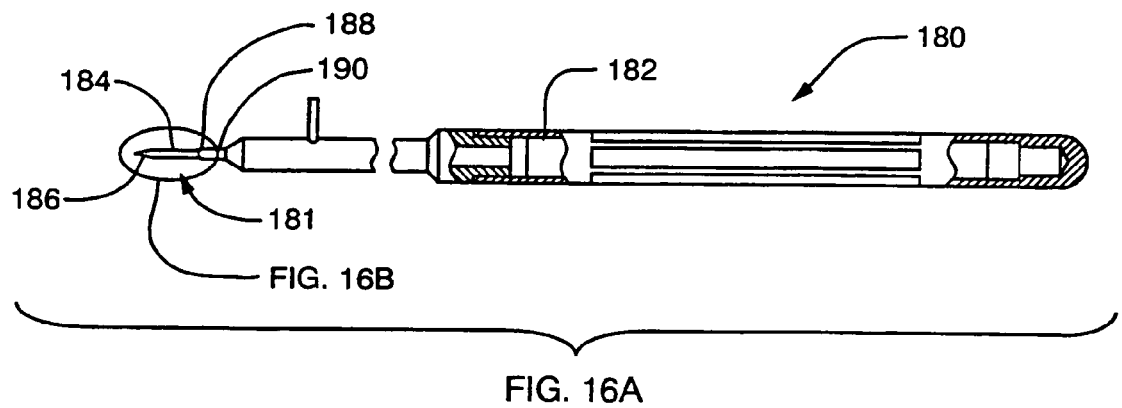
FIG. 16A is a side view of a tissue implant device delivery system.
Figure 16B:
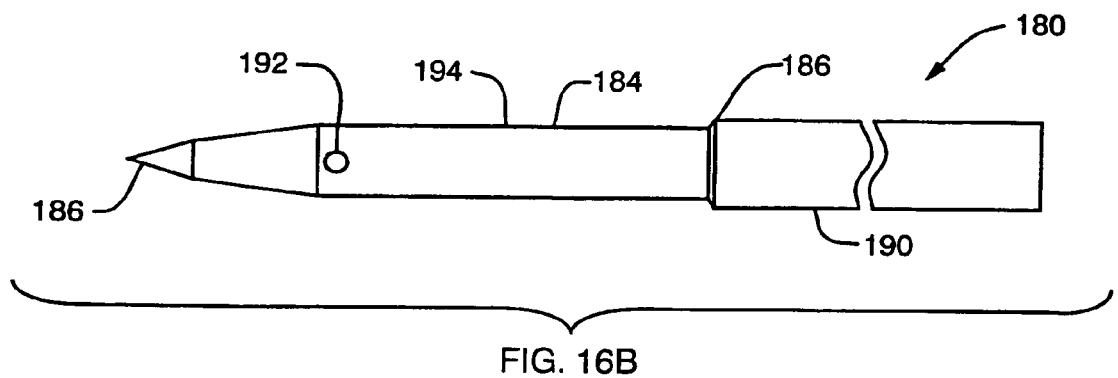
FIG. 16B is a detailed side view of the distal end of the tissue implant device delivery system.
Figure 16C:
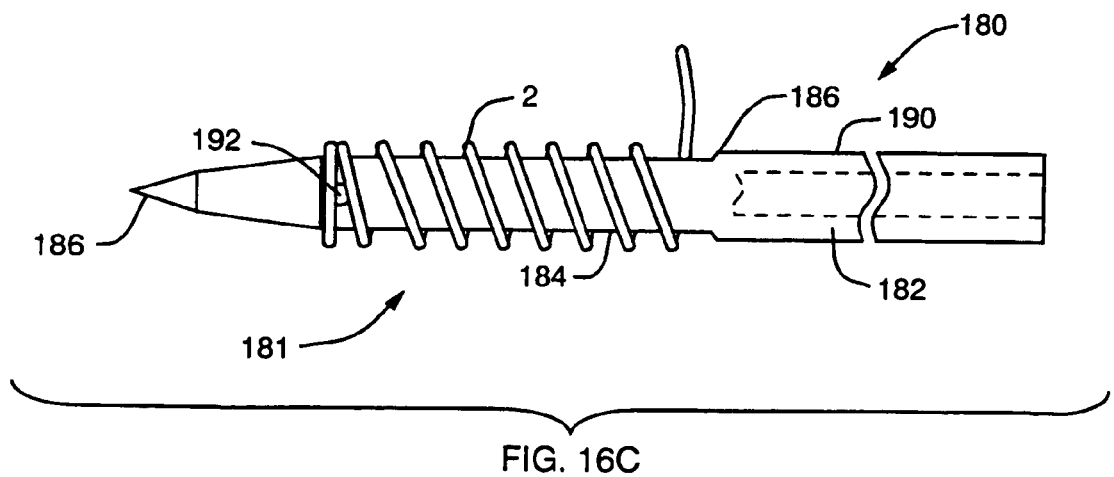
FIG. 16C is a detailed side view of the distal end of the tissue implant device delivery system carrying an implant.

Each of the implant devices of the present invention may be delivered to their intended tissue location surgically. FIGS. 16A–16C show an example of a surgical delivery device that may be used to deliver the implants into tissue such as that of the myocardium of the heart. The delivery device, shown in FIG. 16A, comprises an obturator 180 that includes a main shaft 182, by which it can be gripped and manipulated. The distal end 181 of the shaft 182 is shown in detail in FIG. 16B and includes a reduced diameter device support section 184 having a sharp distal tip 186 adapted to pierce tissue. The diameter of the shaft segment 184 is such as to fit closely within the interior of the devices. The proximal end of the segment 184 terminates in a shoulder 188 formed at the junction of a proximally adjacent, slightly enlarged diameter portion 190 of the shaft. The distal end of the device support segment 184 may include a radially projecting pin 192 dimensioned to project and fit between adjacent turns of the coils of a device. The pin 192 engages the coils in a thread-like fashion so that after the assembly has been inserted into the tissue, the obturator 180 can be removed simply by unscrewing the obturator to free it from the implanted coil. Alternatively, the obturator may be configured without the projecting pin 192 so that the device can be slipped on and off the obturator, without screwing. When an implant device 2 is mounted on the obturator 180, as is shown in FIG. 16C the proximal end of the device may bear against the shoulder 188, and the tail 28, if so equipped may extend along the segment 190 of the obturator.

In use, the intended tissue location is first accessed surgically, such as by a cut-down method. The obturator, with an implant device loaded on to segment 184, then may be advanced into the tissue to deliver the implant. The sharp tip pierces the tissue permitting the obturator and implant to be pushed inward into the tissue. In the example of delivery to the myocardium, the epicardial surface of the heart is accessed and penetrated by the obturator to deliver the implant. The shoulder 188 prevents proximal movement of the implant along segment 184 during delivery. Preferably, the distal end of the obturator is projected to, and slightly beyond, the endocardium to place the implant device. The obturator then may be unscrewed and separated from the implant device. If the obturator is configured without the pin 192, the obturator may be withdrawn directly from the device and the tissue. Simply applying light closure pressure to the epicardial puncture will cause the puncture hole to clot at the epicardium.

An alternative method of anchoring the device comprises applying a surgical adhesive to the site of the implant such that adhesive is joined to the implant device and to surrounding tissue so that it is adhered. As described previously, one method of applying the surgical adhesive may comprise applying it directly at the surgical site or manually or delivering a quantity of surgical adhesive through the obturator delivery device directly to the cavity 14 created in the tissue by the device.

In yet another method of providing a device that resists migration, each of the above described implant embodiments may exhibit improved resistance to migration by being configured to have enhanced axial flexibility. The flexibility may be controlled by a number of factors. One factor in controlling the flexibility of a helical coil device is to decrease the spacing between adjacent coils. Wire diameter may vary between 0.006 inches to 0.010 inches for the above described devices with 0.007 to 0.008 being preferred. Preferred pitch with such diameters may be on the order of 0.25 mm–1 mm. The flexibility of the spring implant may also be increased by increasing the overall diameter of the coils.

Generally, surgical grade stainless steels are used to fabricate the implant devices discussed above, but other materials having different modulii of elasticty such as nickel titanium alloys can be used. Additionally, implants formed from 2 or more different materials can be formed to provide varying flexibility. Different material filaments can be joined by welding or crimping of a malleable sleeve.

From the foregoing it will be appreciated that the invention provides a novel approach to providing an anchoring system for implant devices. The devices and methods of the present invention are simple and easy to apply to a wide range of implant designs.

It should be understood however, that the foregoing description of the invention is intended merely to be illustrative thereof and that other modifications, embodiments and equivalents may be apparent to those who are skilled in the art without departing from its spirit. Having thus described the invention what we desire to claim and secure by letters patent is:

What is claimed is:

1. A myocardial tissue implant device adapted to be implanted in a human myocardium having a predetermined thickness at an implant site, the implant being configured to resist migration and comprising:
    an elongate flexible body having proximal and distal portions, the proximal portion, prior to implantation, having a larger profile than the distal portion,
    the flexible body defining an exterior, a hollow interior, and at least one opening between the interior and exterior, and a tail at the proximal portion,
    the length of the implant being less than said predetermined thickness whereby the implant device may be implanted within the myocardium with at least part of the tail disposed below the external surface of the myocardium and the distal portion being disposed proximally of the innermost surface of the myocardium.

2. A tissue implant device as defined in claim 1 wherein the device is configured to resist migration by exhibiting longitudinal flexibility to substantially absorb migratory forces placed on it by the surrounding tissue.

3. A tissue implant device as defined in claim 2 wherein the flexible body comprises a helical spring.

4. The myocardial tissue implant device of claim 1, further comprising a surgical adhesive applied to the device.

5. A tissue implant device as defined in claim 4 wherein the surgical adhesive is associated with the device after the device is implanted in tissue.

6. A myocardial tissue implant device adapted to be implanted in a human myocardium having a predetermined thickness at an implant site, the implant being configured to resist migration comprising:
    an elongate flexible body having proximal and distal portions, the proximal portion, prior to implantation, having a larger profile than the distal portion,
    a tail at the proximal portion,
    the length of the implant being less than said predetermined thickness whereby the implant device may be implanted within the myocardium with at least part of the tail disposed below the external surface of the myocardium and the distal portion being disposed proximally of the innermost surface of the myocardium.

7. A tissue implant device as defined in claim 6 wherein the tail defines a profile that is larger than the distal portion of the body.

8. A tissue implant device as defined in claim 7 wherein the tail is configured to remain at the tissue surface when the device is implanted.

9. A tissue implant device as defined in claim 8 wherein the tail comprises a broadly wound most proximal coil of the spring having a diameter that is greater than the diameter of coils of the body of the device.

10. A tissue implant device as defined in claim 9 wherein the broadly wound coil is concentric with the body of the device.

11. A tissue implant device as defined in claim 9 wherein the broadly wound coil has a center which is offset from the longitudinal axis of the body of the device.

12. A tissue implant device as defined in claim 9 wherein the tail includes a proximal end of the spring and the proximal end is secured to the broadly wound coil.

13. A tissue implant device as defined in claim 12 wherein the proximal end is joined to the broadly wound coil by being wrapped around the loop.

14. A tissue implant device as defined in claim 13 wherein the proximal end of the spring extends distally from the broadly wound coil after it has been wrapped about the broadly wound coil to serve as a barb.

15. A tissue implant device as defined in claim 12 wherein the proximal end is joined to the broadly wound coil by welding.

16. A tissue implant device as defined in claim 12 wherein the proximal end of the spring is joined to the broadly wound coil by a malleable sleeve crimped around the proximal end and broadly wound coil to secure the proximal end to the coil.

17. A tissue implant device as defined in claim 12 wherein the broadly wound coil is joined to the body of the device by a neck portion.

18. A tissue implant device as defined in claim 17 wherein the neck comprises at least one straight segment.

19. A tissue implant device as defined in claim 17 wherein the neck comprises a coil lying in a plane that is substantially parallel to the longitudinal axis of the device.

20. A tissue implant device as defined in claim 9 wherein the broadly wound coil is non-circular.

21. A tissue implant device as defined in claim 7 wherein the tail is configured to be implanted in the tissue when the body of the device is implanted.

22. A tissue implant device as defined in claim 21 wherein the tail is formed by a more broadly wrapped coil adjacent to the proximal portion of the body forming an arm that extends laterally from the longitudinal axis of the device in the diameter of coils that comprise the body of the spring.

23. A tissue implant device as defined in claim 22 wherein the flexible body comprises a helical spring and the tail is deformed to be out of plane with the helical orientation of coils comprising the body of the spring.

24. A method of implanting a device in a wall of tissue comprising:
providing an implantable device having an elongate flexible body with proximal and distal ends and an anchoring tail at the proximal end that defines a larger profile than the distal end of the implant, the length of the implantable device being less than the thickness of the tissue wall whereby the device may be implanted within the wall with at least part of the tail disposed below one surface of the wall and the distal portion of the implant being disposed within the wall and spaced from the opposite surface of the wall;
providing an elongate implant delivery device having a sharp tip configured to penetrate tissue and releasably retain the tissue implant device;
associating the implantable device with the implant delivery device;
accessing the desired tissue implant site;
applying a penetrating force to the implant and implant delivery device combination such that the combination penetrates tissue to implant the device within the tissue wall;
withdrawing the implant delivery device from the implanted device.

25. A method as defined in claim 24 wherein the implant device and delivery device combination is rotated while penetrating forces are applied to screw the device into the tissue.

26. A method as defined in claim 25 wherein the tail of the implant device is submerged below the surface of the tissue after implantation.

27. A method as defined in claim 25 wherein the tail of the implant device remains exposed at the surface of the tissue after implantation.

28. A method of implanting a tissue implant device to promote angiogenesis within a tissue comprising:
providing an implantable device configured to be anchored within tissue so that it does not migrate from the tissue after implantation comprising an elongate flexible body having proximal and distal portions each defining a profile, the proximal portion having a larger profile than the distal portion and a tail,
inserting the distal portion of the device into the tissue and advancing the device to embed the device in the tissue with the distal end of the device covered by the tissue and the tail at the proximal portion being embedded below the tissue surface.

29. A method of implanting a tissue implant device as defined in claim 28 wherein the device is delivered percutaneously.

30. A method of implanting a tissue implant device as defined in claim 28 wherein the device is delivered transthoracically to the intended tissue location.

31. A method of delivering a tissue implant device as defined in claim 28 wherein the device is delivered surgically to the intended tissue location.

32. A method of anchoring a tissue implant device within tissue comprising:
providing an implantable body having a proximal portion and a distal portion each defining a profile and wherein the profile of the proximal portion is larger than that of the distal portion and the proximal portion comprises a tail;
providing a delivery device configured to carry the implantable body to an intended tissue location and implanting the device in tissue;
associating the body with the delivery device and implanting the body in tissue at the intended location to a depth so that the tail is embedded below the tissue surface and the distal end of the device is enclosed within tissue;
applying a surgical adhesive at the site of the implant to secure the body to the tissue.

33. A method of implanting an implant device as defined in claim 32 wherein the surgical adhesive is applied to the implant site by the delivery device after implantation.

34. A method of delivering an implant device as defined in claim 32 wherein the surgical adhesive is applied to the body prior to implantation.

35. A method of implanting an implant device configured to resist migration in tissue comprising:
providing a flexible spring body implant device having proximal and distal portions, the proximal portion, prior to implantation, having a larger profile than the distal portion, the implant device having sufficient longitudinal flexibility to absorb migratory forces applied on the device by surrounding tissue after implantation;

inserting the flexible spring body into tissue to a depth such that the distal portion is enclosed by the tissue.

36. A myocardial tissue implant device adapted to be implanted, at an implant site, in a human myocardium comprising:

an elongate flexible body having proximal and distal portions, the proximal portions, prior to implantation, having a larger profile than the distal portion, wherein the flexible body comprises a helical spring and a tail at the proximal portion, the length of the implant being less than the wall thickness of the myocardium at the implant site whereby the implant may be embedded in the myocardium at the implant site with the tail in engagement with the outer surface of the myocardium and the distal portion being fully enclosed by the myocardium.

37. A tissue implant device as defined in claim 36 wherein the helical spring has varying flexibility along its length.

38. A tissue implant device as defined in claim 37 wherein the filament is comprised of a plurality of materials of varying modulii of elasticity.

39. A tissue implant device as defined in claim 37 wherein the varying flexibility is created by varying the distance between individual coils of the helical spring.

40. The tissue implant device as defined in claim 37 wherein the helical spring is formed from a filament having a varying thickness along its length, which creates varying flexibility along the length of the helical spring.

41. A tissue implant device as defined in claim 36 wherein the helical spring is formed from a filament having varying modulus of elasticity.

42. A device as defined in claim 36 wherein individual coils of the helical spring have a constantly increasing diameter from the distal portion to the proximal portion.

43. A tissue implant device as defined in claim 36 wherein coils of the distal portion define a constant diameter and coils of the proximal portion define an increasing diameter in the proximal direction.

44. A tissue implant device as defined in claim 36 wherein the helical spring is formed from a filament having a non-circular cross-sectional shape.

45. A tissue implant device as defined in claim 44 wherein the cross-sectional shape of the filament is rectangular.

46. A tissue implant device as defined in claim 45 wherein the major axis of the rectangular cross-section is substantially perpendicular to the longitudinal axis of the device.

47. A tissue implant device as defined in claim 45 wherein the major axis of the rectangular cross-section is at an acute angle to the longitudinal axis of the device.

* * * * *